US006291634B1

(12) United States Patent
Tanaka et al.

(10) Patent No.: US 6,291,634 B1
(45) Date of Patent: Sep. 18, 2001

(54) POLYAMINO ACID DERIVATIVES

(75) Inventors: Hiroyuki Tanaka; Tatsuru Tabohashi, both of Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/372,144

(22) Filed: Aug. 11, 1999

(30) Foreign Application Priority Data

Aug. 12, 1998 (JP) .................................................. 10-228035

(51) Int. Cl.$^7$ .................................................. C08G 69/10
(52) U.S. Cl. .................................................. 528/328
(58) Field of Search .............................................. 528/328

(56) References Cited

U.S. PATENT DOCUMENTS

| | | |
|---|---|---|
| 3,780,099 | 12/1973 | Scanlon et al. . |
| 3,989,636 | 11/1976 | Domba . |
| 5,849,948 | 12/1998 | Patel et al. . |
| 5,958,869 | 9/1999 | Noguchi et al. . |

OTHER PUBLICATIONS

Derwent Publications Ltd., Derwent Abstracts, AN 1980–01032C, JP 54–148898, Nov. 21, 1979.

Derwent Publications Ltd., Derwent Abstracts, AN 1989–237687, JP 01–172312, Jul. 7, 1989.

Derwent Publications Ltd., Derwent Abstracts, AN 1996–350170, JP 08–165271, Jun. 25, 1996.

*Primary Examiner*—Nathan M. Nutter
(74) *Attorney, Agent, or Firm*—Oblon, Spivak, McClelland, Maier & Neustadt, P.C.

(57) ABSTRACT

Disclosed herein are the novel polyamino acid derivatives characterized in that at least four amino acid molecules are bound through the nitrogen atoms of the amino groups by crosslinking groups (e.g., alkylene groups which may have a hydroxyl group on, and/or an ether linkage in, the carbon chain), and their various uses, as well as the uses of the polyamino acid derivatives having a structure similar to that of the novel polyamino acid derivatives, but wherein less than 4 amino asid molecules are bound in one molecule, as a chelating agent, a pigment dispersant, a surface-treating agent for a powder, toiletries and a rust-proofing agent.

16 Claims, No Drawings

POLYAMINO ACID DERIVATIVES

BACKGROUND OF THE INVENTION

1. Field of the Invention

The present invention relates to novel polyamino acid derivatives. More specifically, the present invention relates to novel polyamino acid derivatives which are useful as a chelating agent for metallic ions such as Ca, Mg, Fe or Cu. The present invention further relates to the use of polyamino acid derivatives, inclusive of such novel polyamino acid derivatives, as 1) a pigment dispersant for paints or inks, 2) a surface-treating agent for a powder used in paints, inks, resin composite materials or toiletries, 3) a humectant in toiletries, or 4) a rust-proofing agent.

2. Discussion of the Background Art

Polyamino acid derivatives obtained by condensing amino acids or derivatives thereof through heat polymerization in such that the amino acids or derivatives thereof are bound through the peptide linkage, have been so far known. For example, polyaspartates have been used as a humectant in toiletries.

An amino acid itself contains both a carboxyl group and an amino group in the molecule, having ampholytic properties. However, since amino acids are bound, as just described, through the peptide linkage in a polyamino acid known so far, properties inherent in amino acids, for example, ampholytic properties, have been lost.

Meanwhile, it is disclosed in JP-A-9-194448 that amino acid derivatives (diamine-type polyamino acids) in which two molecules of an amino acid are bound to one molecule of a dihaloalkane or epichlorohydrin are useful as a highly biodegradable chelating agent. Further, it is disclosed in U.S. Pat. No. 3,989,636 that a copolymer of glycine or aspartic acid and epichlorohydrin (degree of polymerization n=2 to 3) has a chelating activity.

Thus, those compounds in which two or three amino acid molecules are bound through other than the peptide linkage are indeed known, but no higher-molecular compounds have actually produced and examined upon the properties thereof. And, none of the polyamino acid derivatives already known have been applied as any agents other than the chelating agent.

SUMMARY OF THE INVENTION

Under these circumstances of the background art, it is an object of the present invention to provide novel polyamino acid derivatives that can find a wide variety of uses. It is another object of the present invention to provide the novel uses of known polyamino acids.

In view of the above, the present inventors have assiduously conducted investigations, and have consequently found that a novel polyamino acid derivative characterized in that at least four amino acid molecules are bound by crosslinking groups through the nitrogen atoms of the amino groups, is excellent in dispersing activity when it is used as a pigment dispersant for paints, inks or the like, excellent in dispersing activity and providing a good touch when it is used as a surface-treating agent for a powder, excellent in chelating force when it is used as a chelating agent for metallic ions, excellent in providing a moistness to the hair or the skin when it is used in toiletries, and excellent in rust-proofing force for a metal, and that a polyamino acid derivative which has the same chemical structure as the above-mentioned novel amino acid derivative except that the number of amino acids is less than 4 and of which the use has been unknown other than as a chelating agent, is also useful as a pigment dispersant, a surface-treating agent, a toiletry ingredient or a rust-proofing agent. Such findings have led to the completion of the invention.

Accordingly, the present invention relates to novel polyamino acid derivatives characterized in that at least four amino acid molecules are bound by crosslinking groups through the nitrogen atoms of the amino groups, and to the novel uses of polyamino acid derivatives including the novel polyamino acid derivatives.

DETAILED DESCRIPTION OF THE INVENTION

The invention will be described in detail below.

First, the novel polyamino acid derivatives per se of the present invention will be described.

The novel polyamino acid derivatives of the present invention are, as has been described above, polyamino acid derivatives in which at least four amino acid molecules are bound by crosslinking groups through the nitrogen atoms of the amino groups.

As such polyamino acid derivatives, for example, those polyamino acid derivatives in which the crosslinking groups are alkylene groups which may have a hydroxyl group on, and/or an ether linkage in, the carbon chain, can be mentioned. Among such alkylene groups, a simple alkylene group is represented by Formula (1) below. An alkylene group having a hydroxyl group on the carbon chain is represented by, for example, Formula (2) below. And, an alkylene group having an ether linkage in the carbon chain is represented by, for example, Formula (3) below. According to the present invention, an alkylene group having an ether linkage in the carbon chain refers to an alkylene group of the structure in which some of the carbon atoms in the carbon chain of the alkylene group is or are replaced with oxygen atom(s).

(1)

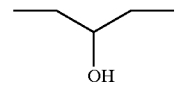

(2)

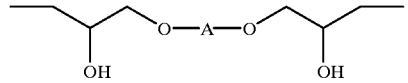

(3)

wherein k in Formula (1) is an integer of from 1 to 10, and A in Formula (3) is, e.g., a group represented by any one of Formulas (4) to (6) below.

(4)

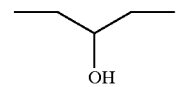

(5)

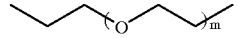

(6)

wherein j in Formula (4) is an integer of from 1 to 10, and m in Formula (6) is an integer of from 1 to 15.

Next, it will be described how to produce the novel polyamino acid derivatives of the present invention.

The novel polyamino acid derivatives of the present invention can be obtained, for example, by reacting epichlorohydrin and/or a polyepoxy compound or a dihaloalkane with an amino acid.

The polyepoxy compound used in the synthetic reaction of a novel polyamino acid of the present invention can be a compound having two or more oxirane groups. Specific examples of the epoxy compound include aliphatic polyepoxy compounds such as ethylene glycol diglycidyl ether, diethylene glycol diglycidyl ether, polyethylene glycol diglycidyl ether, glycerin triglycidyl ether, glycerin diglycidyl ether, sorbitol polyglycidyl ether, pentaerythritol polyglycidyl ether, diglycerin polyglycidyl ether and hexanediol diglycidyl ether; and aromatic polyepoxy compounds such as hydroquinone diglycidyl ether, bisphenol A diglycidyl ether and epoxy novolak. These can be used either singly or in combination of two or more thereof. Further, the polyepoxy compound can be a commercial product. It can also be formed by heating a polyol compound having two or more hydroxyl groups and epichlorohydrin in the presence of a basic catalyst such as sodium hydroxide.

Examples of the amino acid to be used in the synthesis of the novel polyamino acid derivatives of the present invention include acidic amino acids such as glutamic acid and aspartic acid; basic amino acids such as lysine, arginine and ornithine; and neutral amino acids such as glycine, alanine, β-alanine, γ-aminobutyric acid, valine, leucine, isoleucine, serine, threonine, phenylglycine, phenylalanine and tryptophan. These amino acids can be used either singly or in combination of two or more thereof.

When a basic amino acid is used in producing a novel polyamino acid derivative of the present invention, a polyamino acid derivative of a higher molecular weight can more easily be obtained because a basic amino acid has a larger number of free amino groups per a molecule. When an acidic or neutral amino acid is used in producing a novel polyamino acid derivative, a novel polyamino acid derivative of a higher molecular weight can be obtained, when it is used in combination with a basic amino acid.

The amino acid to be used for the synthesis of the novel polyamino acid derivatives of the present invention can be an L-isomer, a D-isomer or a racemic modification. Among them, a racemic modification or an L-isomer is preferable because it can easily be obtained industrially, and of the two, an L-isomer is more preferable in view of the biodegradability of the product.

The reaction of epichlorohydrin and/or a polyepoxy compound with an amino acid (synthetic reaction of the novel polyamino acid derivative of the present invention) can be conducted at from 0 to 200° C., preferably at from 40 to 150° C. When it is conducted at a temperature below 40° C., especially below 0° C., the reaction proceeds slowly, and the reaction time is prolonged. Whereas, when it is conducted at a temperature above 150° C., especially above 200° C., the product gets colored. In order to inhibit the coloration, the reaction may be conducted in a nitrogen stream.

With respect to the reaction ratio of epichlorohydrin and/or a polyepoxy compound to an amino acid, it is advisable that, per x moles of epichlorohydrin and y moles of an polyepoxy compound having z epoxy functional groups, an amino acid is used in an amount of between $2/3 \times (x+y \times z/2)$ and $4/3 \times (x+y \times z/2)$ moles, preferably between $3/4 \times (x+y \times z/2)$ and $5/4 \times (x+y \times z/2)$ moles. When the amino acid is used in an amount of less than $3/4 \times (x+y \times z/2)$ or more than $5/4 \times (x+y \times z/2)$ moles, especially less than $2/3 \times (x+y \times z/2)$ or more than $4/3 \times (x+y \times z/2)$ moles, a lower molecular compound is formed in a large amount.

Incidentally, the (diamine-type) polyamino acid described in JP-A-9-194448 referred to above is obtained by reacting epichlorohydrin and amino acid as starting materials in the same manner as in the present invention. In this case, the number of the amino acids contained in one molecule of the resultant polyamino acid is 2 (two amino acid molecules).

To describe in greater detail, according to the description of the patent document, a dihaloalkane or epichlorohydrin is used in an amount of between 0.5 and 10 moles, preferably between 1 and 5 moles per one mole of the amino acid (paragraph 0017 of the document). The reaction is monitored through HPLC, the reaction is terminated when the amino acid disappears, and the dimer is isolated through crystallization (paragraph 0035 of the document). Meanwhile, according to the present invention, in order to obtain a higher molecular compound in which the number of the amino acids contained in one molecule of the resultant compound is more than 2, it is preferable that the ratio of both starting materials to be subjected to the reaction is 1:1 (molar ratio) as much as possible. Further, the reaction is conducted for a longer period of time to provide a higher molecular weight.

The synthetic reaction of the novel polyamino acid derivatives of the present invention is preferably conducted under alkaline conditions using a base. Specifically, in the reaction of p moles of an amino acid and q moles of epichlorohydrin, it is preferable to use a base in an amount of from 0 to (2p+q+2) moles. It is more preferable to use a base in an amount of (a) from (2p+q) to (2p+q+1) moles in the case of an acidic amino acid, (b) from (p+q) to (p+q+1) moles in the case of a neutral amino acid, and (c) from q to (p+q+1) moles in the case of a basic amino acid. And, in the reaction of r moles of an amino acid and s moles of a polyepoxy compound, it is preferable to use a base in an amount of from 0 to (2r+1) moles. It is more preferable to use a base in an amount of (a) from 2r to (2r+1) moles in the case of an acidic amino acid, (b) from r to (r+1) moles in the case of a neutral amino acid, and (c) from 0 to (r+1) moles in the case of a basic amino acid. When epichlorohydrin and a polyepoxy compound are used in combination, it is advisable to determine the amount of the base according to the molar ratio of the epichlorohydrin to the polyepoxy compound. When the amount of the base is used in an amount of less than the above-described appropriate amounts, the reaction proceeds slowly, and the side reaction occurs. On the contrary, when it is used in an amount of more than the above-described appropriate amounts, on the other hand, epichlorohydrin or the polyepoxy compound may be hydrolyzed, or the product has to be neutralized (post treatment). Thus, either case is undesirable. In the actual operation, it is preferable to carry out the reaction while adjusting the pH to a value of between approximately 8 and 11, more preferably between approximately 9 and 10. Consequently, a higher-molecular-weight polyamino acid derivative can be obtained.

Examples of the base to be used in the synthetic reaction of the novel polyamino acid derivatives of the present invention include alkali metal hydroxides such as sodium hydroxide, lithium hydroxide and potassium hydroxide, and triethanolamine. Of these, the alkali metal hydroxides are preferable because these are compounds which are more basic than the amino group of an amino acid.

In order to decompose epichlorohydrin and/or a polyepoxy compound charged in excess amounts in the reaction system, it is advisable to conduct heating in the presence of such base as referred to above. Consequently, compounds having an epoxy group, such as epichlorohydrin and the polyepoxy compound, are decomposed.

The base to be used in the synthetic reaction of the novel polyamino acid derivatives of the present invention may be used in the form of an amino acid salt resulting from previously reacting a part or the whole of the base with the amino acid.

A polyamino acid copolymer described in U.S. Pat. No. 3,989,636 referred to above is obtained by the reaction of epichlorohydrin and an amino acid as starting materials as in the present invention. It is, however, described that the number of amino acids contained in one molecule of this polyamino acid copolymer is between 2 and 3.

The present inventors have made studies to provide a higher-molecular compound by increasing the number of amino acids contained in one molecule of the polyamino acid derivative, and have consequently found that the effective factors for increasing the number of amino acids include (1) that a pH of a reaction mixture is adjusted to a value of between approximately 8 and 11, more preferably between approximately 9 and 10 during the reaction [an amino acid and a halogen formed during the reaction (in the case of a dihaloalkane or epichlorohydrin) are neutralized], (2) that a crosslinking agent (epichlorohydrin and the like) is added dropwise and the dropwise addition is conducted slowly at that, and (3) that an amine compound is added. They have further found that polyamino acid derivatives having a higher molecular weight in which the number of the amino acids is at least 4 per one molecule exhibit better effects in various uses.

The above-mentioned U.S. patent fails to describe the dropwise addition of epichlorohydrin, the pH adjustment and the amine addition. Further, in the Example where aspartic acid is used, the amount of the base is small, and the reaction is not conducted under satisfactory alkaline conditions. Accordingly, in the polyamino acid copolymer obtained by the procedure described in the U.S. patent, the number of the amino acids is considered to be 2 to 3, as described therein.

The synthetic reaction of a novel polyamino acid derivative of the present invention is ordinarily conducted using a solvent. Examples of such a reaction solvent can be a solvent in which an amino acid and epichlorohydrin and/or a polyepoxy compound can be dissolved or suspended. It is advisable to use one type or a mixture (mixed solvent) of two or more types selected from monohydric alcohols such as methanol, ethanol and isopropanol, polyhydric alcohols such as glycerin and ethylene glycol, polyethers such as ethylene glycol, propylene glycol and ethylene glycol monomethyl ether, ketones such as acetone and methyl ethyl ketone, amides such as dimethylformamide and N-methylpyrrolidone, esters such as ethyl acetate and methyl formate, dimethyl sulfoxide and water.

When a novel polyamino acid derivative of the present invention is produced, an amine compound may be added, as described above, whereby a high-molecular compound can be obtained more easily. This is presumably because the amine compound is incorporated into the novel polyamino acid derivative of the present invention by being reacted with a part of the epichlorohydrin and/or the polyepoxy compound through the amino group(s) thereof.

Examples of such amine compounds to be used according to the present invention include aliphatic polyamines such as ethylenediamine, triethylenetetramine, polyethyleneimine, polyallylamine and polyvinylamine, and primary monoamines such as ammonia, methylamine and ethylamine.

Examples of the dihaloalkane to be used in the production of the novel polyamino acid derivatives of the present invention by the reaction of a dihaloalkane and an amino acid include lower dihaloalkanes such as dichloroethane, dibromoethane, dichloropropane and dibromopropane. Examples of the amino acid are the same as those described earlier.

Such reaction can be conducted, for example, in the following manner. That is, the dihaloalkane and the amino acid are subjected to the dehydrohalogenation reaction from the halogen atom of the former and the hydrogen atom of the amino group of the latter in the presence of a base such as sodium hydroxide.

The thus-obtained novel polyamino acid derivatives of the present invention are obtained as a salt of the base used when the amino acid is used, for example, a neutral or acidic amino acid. This salt can be formed into a free acid by being treated with an acid or a salt of another counter ion such as a salt of another metal by the metal moiety exchange reaction, as required, depending on the use.

Thus, the novel polyamino acid derivative of the present invention includes polyamino acid derivatives represented by any one of Formulas (7) to (9) below.

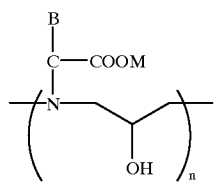

(7)

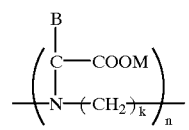

(8)

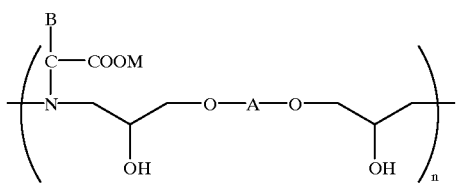

(9)

In the formulas, B represents an amino acid side chain (i.e., a residue left when the a-carbon atom has been removed from an amino acid molecule along with the amino group and the carboxyl group bound thereto; in the case of an acidic amino acid, B itself contains a structure of —COOM), M represents a hydrogen atom or a counter ion, namely an alkali metal such as sodium or potassium, an alkaline earth metal such as magnesium or calcium, a typical metal such as aluminum or zinc, a transition metal such as iron, nickel, ruthenium, rhodium, palladium or platinum, or a quaternary amine such as protonated triethanolamine, diethanolamine, monoethanolamine, triethylamine, diethylamine, monoethylamine, dimethyllaurylamine, or ammonia, n is an integer of 4 or more, k is an integer of from 1 to 10, and A is a group represented by any one of Formulas (4) to (6) above. For the use intended by the present invention, it is preferable that M is a hydrogen atom, an alkali metal or a quaternary amine.

The number average molecular weight by the NMR spectroscocopy of the novel polyamino acid derivatives of the present invention is preferably 100,000 or less, more preferably 10,000 or less. When the number average molecular weight is more than 100,000, the stability in a solvent such as water or alcohol sometimes lacks.

Further, the novel polyamino acid derivative of the present invention can be used under various pH values. The pH may be adjusted when this polyamino acid derivative is used or previously, with an inorganic acidic substance such as hydrochloric acid, sulfuric acid, nitric acid or phosphoric acid, an organic acidic substance such as citric acid, oxalic acid, succinic acid or malic acid, an inorganic basic substance such as sodium hydroxide, potassium hydroxide, lithium hydroxide or magnesium hydroxide, or an organic basic substance such as triethanolamine, triethylamine or ammonia.

Next, it will be described how to use the novel polyamino acid derivatives of the present invention.

The novel polyamino acid derivative of the invention can be used, as noted above, as a surface-treating agent for a powder, a pigment dispersant for paints or inks, a chelating agent for metallic ions, toiletries or a rust-proofing agent. Especially, the novel polyamino acid derivative when produced with the use of an acidic amino acid is useful as a dispersant (inorganic pigment), a surface-treating agent (inorganic pigment), a chelating agent (Ca, Mg or the like) or toiletries (humectant). Meanwhile, the novel polyamino acid derivative when produced with the use of a basic amino acid is useful as a dispersant (organic pigment), a surface-treating agent (organic pigment), a chelating agent (Fe, Cu or the like) or toiletries (hair treatment).

The dispersant of the present invention contains, as an active ingredient, the novel amino acid derivative of the present invention described above. The dispersant of the present invention can be utilized in various fields where a powder is used. It can be utilized to disperse a powder in resin composite materials, paints, inks and toiletries. Such resin composite materials are used as a material for automobile parts, or electrical or electronic-mechanical parts and structural materials. Paints and inks are, for coloration or recording, used by being coated on paper, plastics or timbers. For toiletries, it is used for dispersing the powder in foundations, milky lotions or lipsticks.

When the novel polyamino acid derivative of the present invention is used as a dispersant, the amount thereof is between 0.01 and 200% by weight, calculated as (i.e., in terms of) the novel polyamino acid derivative, based on the powder.

Examples of the powder which is to be dispersed with the use of the dispersant of the present invention include inorganic pigments such as titanium dioxide, iron oxide, cadmium sulfide, calciumcarbonate, bariumcarbonate, bariumsulfate, clay, talc, yellow lead oxide and carbon black; and organic pigments such as azo, diazo, condensed azo, thioindigo, indanthrone, quinacridone, anthraquinone, benzoimidazolone, perylene, pelynone, phthalocyanine, halogenated phthalocyanine, anthrapyridine and dioxazine pigments.

As has been described above, a polyamino acid derivative obtained by using an acidic amino acid has a good affinity for such inorganic pigments, and a novel polyamino acid derivative obtained by using a basic amino acid has a good affinity for such organic pigments.

Resin composite material herein means one which is composed of a resin and a powder. As the resin, various resins are available. Examples thereof include thermoplastic resins such as polyethylene, polypropylene, polyvinyl chloride, polystyrene and an acrylonitrile-butadiene-styrene copolymer; thermosetting resins such as an acrylic resin, an unsaturated polyester, an epoxy resin, a urethane resin and a phenolic resin. Examples of the powder are the same as those which are to be dispersed with the use of the dispersant of the present invention.

When the novel polyamino acid derivative of the present invention is used for the resin composite material, resin additives such as an antioxidant, a lubricant or a flame retardant may be used together therewith, as required or desired.

Paints and inks herein mean, for example, (color) paints, printing inks and copying toners for coloration or recording. The paints and the inks of the present invention are the same as the ordinary paints and inks in their composition and the method for producing the same, except that they contain the pigment dispersant of the present invention. Paints and inks are, as is well known, formed of a resin, a pigment, a pigment dispersant, an organic solvent and other appropriate additives.

Since the novel polyamino acid derivative of the present invention has a high hydrophilicity, it has a good compatibility with paints and inks such as an emulsion paint, an emulsion ink, a water-soluble paint and a water-soluble ink in particular.

Color paint is produced by adding a powder (pigment) to a film-forming main element such as a resin, a film-forming secondary element to be added to the main element in a small amount [both elements are collectively called a film element (non-volatile content)] and a film auxiliary element of a solvent or a diluent [both a film element and a film auxiliary element are collectively called a transparent paint (vehicle)] and kneading the mixture. Ink is produced by adding a pigment to a vehicle obtained by dissolving a resin in a solvent. Copying toner is produced by kneading a resin and a magnetic material.

According to the present invention, excellent paints and inks can be produced by adding the novel polyamino acid derivative of the present invention to these compositions.

Examples of the resin to which the dispersant of the present invention is to be applied in the paints and the inks include a wide variety of resins such as an alkyd resin, a polyester resin, an acrylic resin, an epoxy resin, a polyurethane resin, a silicone resin, a fluororesin, a melamine resin, a benzoguanamine resin, a urea resin, a polyamide resin, a phenolic resin, vinyl chloride and a polyethylene resin.

The dispersant of the present invention can be kneaded with a pigment, a resin, a solvent and other additives to directly form a pigment-containing resin composition. Or, it is also possible that this dispersant is formed into a so-called pigment dispersion base, and a paint or an ink is produced using this pigment dispersion base, a resin, a solvent and the like.

The pigment dispersion base may be composed of three components, namely, the pigment dispersant of the present invention, a pigment and an organic solvent, or it may be composed of these three components and a part or the whole of a dispersion resin (film-forming resin), or of these and additives such as a defoamer, a surface modifier and the like, as in the ordinary pigment dispersion base.

The pigment dispersion base of the present invention can be used as a paint by further adding a dispersion resin or other resins, or can be used directly as a paint or an ink.

Examples of the solvent used in paints and inks include hydrocarbon solvents such as toluene, xylene, high-boiling petroleum hydrocarbon, n-hexane, cyclohexane and n-heptane; halogenated hydrocarbon solvents such as methylene chloride, chloroform and dichloroethane; ether solvents such as dioxane, tetrahydrofuran, butyl ether, butylethyl ether and diglyme; ketone solvents such as methyl isobutyl ketone, cyclohexanone and isophorone; ester solvents such as ethyl acetate, butyl acetate, ethylene glycol monoethyl ether acetate and 2-methoxypropyl acetate; alcohol solvents such as methyl alcohol, ethyl alcohol, n-propyl alcohol, isopropyl alcohol, n-butyl alcohol, isobutyl alcohol, t-butyl alcohol, amyl alcohol, n-hexyl alcohol, n-heptyl alcohol, 2-ethylhexyl alcohol, lauryl alcohol, stearyl alcohol, cyclopentanol, cyclohexanol, benzyl alcohol and p-t-butylbenzyl alcohol; alkylene glycol monoether solvents such as ethylene glycol monomethyl ether, ethylene glycol monoethyl ether, ethylene glycol monobutyl ether, propylene glycol monomethyl ether, propylene glycol monoethyl ether and propylene glycol monobutyl ether; amide solvents such as dimethylacetamide and dimethylformamide; and water. These are appropriately selected depending on the use of the pigment dispersion base, the paints and the inks. These can be used either singly or in combination of two or more thereof.

The pigment dispersion base, the paints and the inks as mentioned above can be produced by dispersing the predetermined starting materials using a roll mill, a ball mill, a sand grinding mill, a paint shaker, a kneader, a dissolver and an ultrasonic dispersing machine, depending on the use of the pigment dispersion base, the paints and the inks.

In this case, a surface-treated powder to be described later may be kneaded with the resin, or an integral blending method in which a pigment dispersant, a powder and a resin are kneaded at the same time may also be employed.

The paints and the inks of the present invention can be put in distribution at concentrations at which these can be used as such by adjusting the amount of the organic solvent in the production thereof as required. Alternatively, these can be put in distribution in the form of a concentrate and be used such that a consumer uses the same at appropriate concentrations by dilution with a solvent.

The surface-treated powder of the present invention means a powder which has been surface-treated with the novel polyamino acid derivative of the present invention. Such a treated powder can be used in various fields such as paints, inks, resin composite materials and toiletries. The surface-treating method is itself not particularly limited, and the surface treatment can be conducted according to a method which is ordinarily employed for the surface treatment of a powder. A dry method using a Henschel mixer, a ball mill, an atomizer, a colloid mill or a Banbury mixer and a wet solvent method in which the surfaces are treated in a solvent and the solvent is then removed can be used as required. Examples of the solvent to be used for the wet solvent method include alcohols such as isopropanol and butanol; ethers such as ethyl cellosolve and butyl cellosolve; ketones such as methyl ethyl ketone and acetone; esters such as ethyl acetate and butyl acetate; and water.

When the surface-treated powder of the present invention is produced, the novel polyamino acid derivative is used in an amount of from 0.01 to 200% by weight based on the powder.

The powder to be subjected to such surface treatment is not particularly limited, and it can be the same as the powder which is to be dispersed with the use of the dispersant of the present invention as described earlier. Examples thereof include inorganic pigments such as titanium dioxide, iron oxide, cadmium sulfide, calcium carbonate, barium carbonate, barium sulfate, clay, talc, yellow lead oxide and carbon black; and organic pigments such as azo, diazo, condensed azo, thioindigo, indanthrone, quinacridone, anthraquinone, benzoimidazolone, perylene, pelynone, phthalocyanine, halogenated phthalocyanine, anthrapyridine and dioxazine pigments.

The chelating agent of the present invention means one which contains, as an active ingredient, the novel polyamino acid derivative of the present invention. The chelating agent of the present invention can be used in all fields in which metallic ions such as Ca, Mg, Fe and Cu have to be formed into a chelate (compound). It can be used in a detergent, cooling water treatment, boiler water treatment, desalination and a flash evaporator.

The amount of the chelating agent of the present invention varies with the amount of the metallic ions present in water. In the case of Ca ions, it is advisable to use the chelating agent in an amount of from 1 to 2,000 mg, calculated as (i.e., in terms of) the solid content, per one gram of the Ca ions.

The toiletry of the present invention which contains the novel polyamino acid derivative of the present invention, and therefore, can give a moistness to the hair or the skin, can be prepared into various forms. The novel polyamino acid derivative can be incorporated in various toiletries (toiletry compositions), for example, hair products such as a shampoo, a rinse, a treatment, a hair conditioner and a hair lotion; basic products such as a cleansing cream and a massage cream; body wash such as a body shampoo; disinfectant detergents; kitchen detergents; and washing detergents. All these products make use of the characteristics of the novel polyamino acid derivative of the present invention that it imparts a moistness to the hair or the skin.

The novel polyamino acid derivative obtained from an acidic amino acid is excellent in moistness in particular, whereas the novel polyamino acid derivative obtained by using a basic amino acid moisturizes the hair, gives a gloss to the hair, makes it easy to arrange the hair and also provides a treatment effect.

The amount of the novel polyamino acid derivative of the present invention in these toiletries (compositions) can be appropriately determined, depending on the use and the formulation. Its ratio occupying a toiletry is usually between 0.1 and 95% in terms of a weight ratio.

It is of course possible that a surfactant ordinarily used in toiletries is added to such toiletries (compositions) unless the effects of the present invention are impaired. Examples thereof include anionic surfactants such as higher fatty acid, polyoxyalkyl ether sulfate, N-acylamino acid carboxylate, polyoxyethylene alkyl ether carboxylate, N-acyl taurine salt, sulfosuccinic acid-based surfactants; amphoteric surfactants such as alkyl dimethylaminoacetic acid betaine, higher fatty acid amidopropyl dimethylaminoacetic acid betaine and imidazoline-based surfactants; nonionic surfactants such as alkyl saccharide-based surfactants, polyoxyethylene alkyl ether-based surfactants, higher fatty acid alkanolamide and amine oxide; and cationic surfactants such as alkyltrimethylammonium chloride and N-acylarginine lower alkyl ester pyrrolidonecarboxylate.

Besides these surfactants, various additives which are ordinarily used in toiletries can be added. Examples thereof include humectants such as ethylene glycol, propylene glycol, 1,3-butylene glycol, glycerin and sorbitol; emulsifier such as glycerol monostearate and polyoxyethylenesorbitan monolaurate; hydrocarbons such as liquid paraffins, vaseline and squalane; esters such as isopropyl myristate and octyldodecyl myristate; cellulose derivatives such as hydroxyethyl cellulose, hydroxypropyl cellulose and carboxymethyl cellulose; anionic polymers such as an acrylic acid-based polymer; various silicone derivatives; and cationic polymers such as a cationic guar gum. Further, preservatives such as paraben derivatives, flavors, pigments, viscosity modifiers, pearling agents, antioxidants, disinfectants, anti-inflammatory agents, ultraviolet absorbers, pH adjusting agents and crude drugs can be incorporated as desired.

The novel polyamino acid derivative of the present invention can be specifically added as a rust-proofing agent to a) a metal working oil (a metal cutting oil, a polishing oil and a rolling oil), b) an industrial lubricant, c) a fuel oil and d) a metal surface protecting agent. More specifically, the metal working oil is used to prevent deterioration of a machine tool by abrasion and to increase a working speed when working a metal, and a rust-proofing property is required for a metal after worked. The industrial lubricant is used to decrease a friction of a portion at which the metal parts of a machine are rotated and rubbed. The rust occurrence involves a serious problem to a machine. The fuel oil is a fuel for automobiles, aircraft and ships, and the rust prevention of the engine room is important. In order to conduct the rust prevention on the metal surface after working the metal for the purpose of protecting the metal surface, a coated film or an oil film is applied thereto.

When the rust-proofing agent of the present invention is used as a) a metal working oil (a metal cutting oil, a polishing oil and a rolling oil), b) an industrial lubricant, c) a fuel oil or d) a metal surface protecting agent, various additives may be added. Examples thereof include surfactants, defoamers, antioxidants, preservatives, anticorrosive agents, organic or inorganic inhibitors, cleaning dispersants, extreme pressure agents (abrasion inhibitors), viscosity index improvers, pour point depressants, fatty acids, fats and oils, and basic compounds.

The surfactants are not particularly limited, and anionic, cationic, nonionic and amphoteric surfactants can be used. Examples of the anionic surfactant include fatty acid-based surfactants such as triethanolamine oleate, sodium laurate, sodium ricinoleate; amino acid-based surfactants such as N-laurylsarcosine sodium salt, sodium N-laurylglutamate and N-laurylglutamic acid triethanolamine salt; sulfonate-based surfactants such as sodium laurylsulfonate, sodium nonylphenylsulfonate and sodium naphthalenesulfonate; phosphate-based surfactants such as sodium 2-ethylhexylphosphate; and sodium naphthenate. Examples of the cationic surfactant include alkylaminotriazoles, alkyloxazolines, alkylamines and amides. Examples of the nonionic surfactant include polyoxyethylene alkylphenyl ethers, polyethylene glycol monofatty acid esters, sorbitan fatty acid esters and polyoxyethylene alkylamides. Examples of the amphoteric surfactant include succinic acid alkyl betaines and N-alkyl triglycines.

The defoamers (antifoaming agents, defoaming agents) are not particularly limited. Examples thereof include silicone-based ones, alcohol-based ones such as oleyl alcohol, polyacrylate-based ones such as polymethacrylates, and phosphate-based ones such as tributyl phosphate.

The antioxidants are not particularly limited. Examples thereof include phenol-based ones such as 2,6-di-tert-butyl-4-methylphenol, amine-based ones such as dioctyldiphenylamine, zinc dithiophosphate-based ones such as zinc diallyl dithiophosphate, and organic sulfur compounds such as dibenzyl sulphide.

The preservatives are not particularly limited. Examples thereof include phenols such as o-phenylphenol and 2,3,4,6-tetrachlorophenol; formaldehyde donors such as 2-hydroxyphenyl-2-nitropropanediol and hexahydro-1,3,5-triethyltriazine; and salicylanilide.

The cleaning dispersants are not particularly limited. Examples thereof include sulfonate-based ones such as calcium alkylbenzenesulfonates, phenate-based ones such as calcium alkylphenol sulfides, succinimide-based ones such as polybutenylsuccinic acid imide, and aralkyl methacrylate-vinylpyrrolidone copolymers.

The extreme pressure agents (abrasion inhibitors) are not particularly limited. Examples thereof include high-molecular fatty acid triglycerides, fatty acid esters, fat and oil polymeric substances, aliphatic amines, higher alcohols, chlorinated products such as chlorinated paraffins, sulfur compounds such as dialkyl disulfides and turpentine sulfide, and zinc dithiophosphate.

The viscosity index improvers are not particularly limited. Examples thereof include compounds such as a polyalkyl methacrylate, polyisobutylene and a polyethylene-polypropylene copolymer.

The pour point depressants are not particularly limited. Examples thereof include a polyalkyl methacrylate and a condensate of a chlorinated paraffin and naphthalene.

The fatty acids are not particularly limited. Examples thereof include oleic acid, stearic acid and lauric acid.

The fats and oils are not particularly limited. Examples thereof include a castor oil, a linseed oil, a lard oil, a whale oil and a soybean oil.

The basic compounds are not particularly limited. Examples thereof include inorganic basic substances such as sodium hydroxide, potassium hydroxide, lithium hydroxide, magnesium hydroxide and calcium hydroxide; and organic basic substances such as triethanolamine, triethylamine and ammonia.

The mechanism how the novel polyamino acid derivative of the present invention is suitable for the above-described uses is considered as follows. For example, in the case of the dispersant, since the polyamino acid derivative of the present invention has a large number of amino groups and carboxyl groups in the molecule, it is adsorbed well onto the surfaces of the pigment, and a satisfactory dispersion state is obtained by electric repulsion. Further, since it is a polymer, the dispersion effect can easily be obtained owing to the steric repulsion.

The present inventors have found, as stated above, that the novel polyamino acid derivatives of the present invention containing at least 4 amino acids in one molecule, find acceptance in the chelating agent, the pigment dispersant, the surface-treating agent of a powder, the humectant of toiletries and the rust-proofing agent. According to the further findings of the present inventors, even when the number (unit number) of amino acids contained in one molecule is from 2 to less than 4, the polyamino acid derivatives having the same structure (U.S. Pat. No. 3,989,636) find acceptance in the same uses. The number of amino acids contained in the polyamino acid is preferably at least 4, more preferably at least 5, still more preferably at least 6, furthermore preferably at least 7, especially preferably at least 8, concerning the above-mentioned uses.

The polyamino acid derivative of the present invention is generally obtained not as a product having a single composition, but as a mixture of derivatives different in the number of amino acids contained in one molecule. The mixture can be used by being purified as a product of a single composition through chromatography. However, it is generally considered that the mixture can be actually used as such. The average number of amino acids per one molecule in the mixture of such polyamino acid derivatives exceeds preferably 3, more preferably 4, still more preferably 5, and especially preferably 6.

EXAMPLES

With respect to the polyamino acid derivatives as such and the dispersant, the surface-treating agent of a powder, the chelating agent and the toiletries obtained by using the polyamino acid derivatives of the present invention, the contents thereof will be described in detail below by referring to the following Examples and Comparative Examples. However, the following Examples do not limit the technical scope of the present invention, but are used only for clarifying the contents of the present invention. Further, "parts" and "%" in Examples are all on the weight basis (i.e., parts by weight and % by weight, respectively), and "mol" means a molar ratio.

Example 1

A reaction flask fitted with a thermometer, a stirrer, a nitrogen introduction inlet and a reflux tube were charged with 29.43 parts (0.2 mols) of glutamic acid (supplied by Ajinomoto), 16.0 parts (0.4 mols) of sodium hydroxide (supplied by Junsei Kagaku) and 200 parts of water. 18.5 Parts (0.2 mols) of epichlorohydrin (supplied by Junsei Kagaku) was quickly added thereto dropwise in a nitrogen stream. The mixture was allowed to stand for 1 hour, and then maintained for 3 hours while being heat-refluxed for reaction. When it was found by the IR (infrared) spectroscopy that the characteristic absorption or band ascribable to the epoxy group had disappeared, then the reaction was terminated. The number average molecular weight (Mn) was calculated from the area measured by the NMR (nuclear magnetic resonance) spectroscopy, and was also measured through GPC (gel permeation chromatography) using PEG (polyethylene glycol) as a standard substance. The thus-obtained compound was a polyamino acid derivative in which the alkylene group was represented by Formula (2) above.

IR (cm$^{-1}$); 3350, 1570, 1410, 1350, 1040.

Mn; 850 (NMR), 800 (GPC).

Example 2

A reaction flask fitted with a thermometer, a stirrer, a nitrogen introduction inlet and a ref lux tube were charged with 29.43 parts (0.2 mols) of glutamic acid (supplied by Ajinomoto), 8.0 parts of sodium hydroxide (supplied by Junsei Kagaku) and 200 parts of water. 18.5 Parts (0.2 mols) of epichlorohydrin (supplied by Junsei Kagaku) was slowly added thereto dropwise in a nitrogen stream while a 27% NaOH aqueous solution was added dropwise to keep the pH at 10. The mixture was allowed to stand for 1 hour, and then maintained for 3 hours while being heat-refluxed for reaction. When it was found by the IR spectroscopy that the characteristic absorption ascribable to the epoxy group had disappeared, then the reaction was terminated. The number average molecular weight (Mn) was measured as in Example 1. The thus-obtained compound was also a polyamino acid derivative in which the alkylene group was represented by Formula (2) above.

IR (cm$^{-1}$); 3350, 1570, 1410, 1350, 1040.

Mn; 3,000 (NMR), 2,800 (GPC).

Example 3

A reaction flask fitted with a thermometer, a stirrer, a nitrogen introduction inlet and a ref lux tube were charged with 54.8 parts (0.3 mols) of lysine hydrochloride (supplied by Ajinomoto), 18 parts (0.45 mols) of sodium hydroxide (supplied by Junsei Kagaku) and 200 parts of water. 27.75 Parts (0.3 mols) of epichlorohydrin (supplied by Junsei Kagaku) was slowly added thereto dropwise in a nitrogen stream while a 27% NaOH aqueous solution was added dropwise to keep the pH at 10. The mixture was allowed to stand for 1 hour, and then maintained for 3 hours while being heat-refluxed for reaction. When it was found by the IR spectroscopy that the characteristic absorption ascribable to the epoxy group had disappeared, then the reaction was terminated. The number average molecular weight (Mn) was calculated from the area measured by the NMR spectroscopy. The thus-obtained compound was a polyamino acid derivative in which the alkylene group was represented by Formula (2) above.

IR (cm$^{-1}$); 3400, 1560, 1470, 1410, 1320, 1025–1125.

Mn; 4,500 (NMR).

Example 4

The same reaction flask as that used in Example 1 was charged with 29.43 parts (0.2 mols) of glutamic acid (supplied by Ajinomoto), 16.0 parts of sodium hydroxide (supplied by Junsei Kagaku) and 200 parts of water. 87.2 Parts (0.4 mols) of diethylene glycol diglycidyl ether "SR-2EG" (supplied by Sakamoto Yakuhin) was quickly added thereto dropwise in a nitrogen stream. The mixture was allowed to stand for 1 hour, and then maintained for 3 hours while being heat-refluxed for reaction. When it was found by the IR spectroscopy that the characteristic absorption ascribable to the epoxy group had disappeared, then the reaction was terminated. The thus-obtained compound was a polyamino acid derivative in which the alkylene group was represented by Formula (3) above and A was the group represented by Formula (6) above.

IR (cm$^{-1}$); 3400, 2860, 1460, 1410, 1350, 1250, 1020–1160 940, 860.

Mn; 750 (NMR).

Example 5

The same reaction flask as that used in Example 1 was charged with 22.07 parts (0.15 mols) of glutamic acid (supplied by Ajinomoto), 16.0 parts of sodium hydroxide (supplied by Junsei Kagaku) and 200 parts of water. 18.5 Parts (0.2 mols) of epichlorohydrin (supplied by Junsei Kagaku) was quickly added thereto dropwise in a nitrogen stream. Further, 9.43 parts (0.05 mols) of lysine hydrochloride (supplied by Ajinomoto) was added thereto. The mixture was allowed to stand for 1 hour, and then maintained for 3 hours while being heat-refluxed for reaction. When it was found by the IR spectroscopy that the characteristic absorption ascribable to the epoxy group had disappeared, then the reaction was terminated. The thus-obtained compound was a polyamino acid derivative in which the alkylene group was represented by Formula (2) above.

IR (cm$^{-1}$); 3300, 2950, 1550, 1410, 1330, 1120, 1040.

Mn; 880 (NMR).

Example 6

The same reaction flask as that used in Example 1 was charged with 29.43 parts (0.2 mols) of glutamic acid (supplied by Ajinomoto), 16.0 parts of sodium hydroxide (supplied by Junsei Kagaku) and 200 parts of water. 18.5 Parts (0.15 mols) of diethylene glycol diglycidyl ether "SR-2EG" (supplied by Sakamoto Yakuhin) was quickly added thereto dropwise in a nitrogen stream. Further, 3.01 parts (0.05 mols) of ethylenediamine (supplied by Sakamoto Yakuhin) was added thereto. The mixture was allowed to stand for 1 hour, and then maintained for 3 hours while being heat-refluxed for reaction. When it was found by the IR spectroscopy that the characteristic absorption ascribable to the epoxy group had disappeared, then the reaction was terminated. The thus-obtained compound was a polyamino acid derivative in which the alkylene group was represented by Formula (3) above and A was the group represented by Formula (6) above.

IR ($cm^{-1}$); 3300, 2900, 1570, 1420, 1340, 1030–1150.

Mn; 4,877 (NMR).

Example 7

The same reaction flask as that used in Example 1 was charged with 20.0 parts (0.15 mols) of aspartic acid (supplied by Ajinomoto), 3.8 parts (0.05 mols) of glycine (supplied by Ajinomoto), 14.0 parts of sodium hydroxide (supplied by Junsei Kagaku) and 200 parts of water. 43.6 Parts (0.2 mols) of diethylene glycol diglycidyl ether "SR-2EG" (supplied by Sakamoto Yakuhin) was quickly added thereto dropwise in a nitrogen stream. The mixture was allowed to stand for 1 hour, and then maintained for 3 hours while being heat-refluxed for reaction. It was found by the IR spectroscopy that the characteristic absorption ascribable to the epoxy group had disappeared, then the reaction was terminated. The thus-obtained compound was a polyamino acid derivative in which the alkylene group was represented by Formula (3) above and A was the group represented by Formula (6) above.

IR ($cm^{-1}$); 3150, 2900, 1560, 1400, 1360, 1250, 1025–1160.

Mn; 1,600 (NMR).

Example 8

The same reaction flask as that used in Example 1 was charged with 17.4 parts (0.1 mols) of arginine (supplied by Ajinomoto), 150 parts of water and 150 parts of isopropyl alcohol (supplied by Junsei Kagaku). 31.6 Parts (0.15 mols) of glycerin diglycidyl ether "SR-GLG" (supplied by Sakamoto Yakuhin) was quickly added thereto dropwise in a nitrogen stream. The mixture was allowed to stand for 1 hour, and then heated to 85° C. for 3 hours while being kept at this temperature for reaction. When it was found by the IR spectroscopy that the characteristic absorption ascribable to the epoxy group had disappeared, then the reaction was terminated. The thus-obtained compound was a polyamino acid derivative in which the alkylene group was represented by Formula (3) above and A was represented by Formula (5) above.

IR ($cm^{-1}$); 3300, 2870, 1680, 1560, 1460, 1360, 1050–1150.

Mn; 604 (NMR).

Example 9

The same reaction flask as that used in Example 1 was charged with 54.8 parts (0.3 mols) of lysine hydrochloride (supplied by Ajinomoto), 36 parts of sodium hydroxide (supplied by Junsei Kagaku) and 200 parts of water. 27.75 Parts (0.3 mols) of epichlorohydrin (supplied by Junsei Kagaku) was quickly added thereto dropwise in a nitrogen stream, and maintained for 3 hours while being heat-refluxed for reaction. When it was found by the IR spectroscopy that the characteristic absorption ascribable to the epoxy group had disappeared, then the reaction was terminated. The thus-obtained compound was a polyamino acid derivative in which the alkylene group was represented by Formula (2) above.

IR ($cm^{-1}$); 3400, 1560, 1470, 1420, 1320, 1025–1125.

Mn; 2,060 (NMR).

Example 10

A reaction flask fitted with a thermometer, a stirrer, a nitrogen introduction inlet and a ref lux tube was charged with 29.43 parts(0.2 mols) of glutamic acid (supplied by Ajinomoto), 8.0 parts of sodium hydroxide (supplied by Junsei Kagaku) and 200 parts of water. 18.5 Parts (0.2 mols) of epichlorohydrin (supplied by Junsei Kagaku) was quickly added thereto dropwise in a nitrogen stream while a 27% NaOH aqueous solution was added dropwise to keep the pH at 10. The mixture was allowed to stand for 1 hour, and then maintained for 3 hours while being heat-refluxed for reaction. When it was found by the IR spectroscopy that the characteristic absorption ascribable to the epoxy group had disappeared, then the reaction was terminated. The number average molecular weight (Mn) was calculated from the area measured by the NMR spectroscopy. The thus-obtained compound was a polyamino acid derivative in which the alkylene group was represented by Formula (2) above.

IR ($cm^{-1}$); 3350, 1570, 1410, 1350, 1040.

Mn; 1,800 (NMR), 2,000 (GPC).

Example 11

A reaction flask fitted with a thermometer, a stirrer, a nitrogen introduction inlet and a reflux tube was charged with 29.43 parts (0.2 mols) of glutamic acid (supplied by Ajinomoto), 16.0 parts (0.4 mols) of sodium hydroxide (supplied by Junsei Kagaku) and 200 parts of water. 18.5 Parts (0.2 mols) of epichlorohydrin (supplied by Junsei Kagak) was very quickly added thereto dropwise in a nitrogen stream. The mixture was allowed to stand for 1 hour, and then maintained for 3 hours while being heat-refluxed for reaction. When it was found by the IR spectroscopy that the characteristic absorption ascribable to the epoxy group had disappeared, and the reaction was terminated. The number average molecular weight (Mn) was calculated from the area measured by the NMR spectroscopy. The thus-obtained compound was a polyamino acid derivative in which the alkylene group was represented by Formula (2) above.

IR ($cm^{-1}$); 3350, 1570, 1410, 1350, 1040.

Mn; 550 (NMR), 500 (GPC).

Example 12

A reaction flask fitted with a thermometer, a stirrer, a nitrogen introduction inlet and a ref lux tube was charged with 29.43 parts (0.2 mols) of glutamic acid (supplied by Ajinomoto), 18.0 parts (0.6 mols) of sodium hydroxide (supplied by Junsei Kagaku) and 200 parts of water. 18.5 Parts (0.2 mols) of epichlorohydrin (supplied by Junsei Kagaku) was quickly added dropwise thereto in a nitrogen stream. The mixture was allowed to stand for 1 hour, and then maintained for 3 hours while being heat-refluxed for reaction. When it was found by the IR spectroscopy that the characteristic absorption ascribable to the epoxy group had disappeared, then the reaction was terminated. The number average molecular weight (Mn) was calculated from the area measured by the NMR spectroscopy. The thus-obtained compound was a polyamino acid derivative in which the alkylene group was represented by Formula (2) above.

IR (cm$^{-1}$); 3350, 1570, 1410, 1350, 1040.

Mn; 880 (NMR).

Evaluation of a Surface-treated Powder

Example 13

70Parts by weight of titanium dioxide "TIPAQUE CR-50" (supplied by Ishihara Sangyo) was mixed with a mixture of 2 parts by weight (in terms of the solid content) of the polyamino acid derivative obtained in Example 1 and 10 parts by weight of methanol (supplied by Junsei Kagaku). The resulting mixture was stirred with the use of a Henschel Mixer (supplied by Mitsui Mining & Smelting) for 10 minutes, and dried with the use of a vacuum drier for 2 hours to obtain a surface-treated powder.

With respect to the surface-treated powder, the oil absorption (unit: mg/100 g) was measured using a liquid paraffin (supplied by Junsei Kagaku). Further, the touch (moist touch) of the powder was evaluated according to the following four grades.

⊚: moist

○: somewhat moist

Δ: moderate x: poor

The results are shown in Table 1 below.

Example 14

Example 13 was repeated except that the polyamino acid derivative obtained in Example 4 was used instead of the polyamino acid derivative obtained in Example 1 to obtain a surface-treated powder. This surface-treated powder was subjected to the same measurement and evaluation as in Example 13. The results are shown in Table 1 below.

Example 15

Example 13 was repeated except that the polyamino acid derivative obtained in Example 6 was used instead of the polyamino acid derivative obtained in Example 1 to obtain a surface-treated powder. This surface-treated powder was subjected to the same measurement and evaluation as in Example 13. The results are shown in Table 1 below.

Example 16

Example 13 was repeated except that the polyamino acid derivative obtained in Example 8 was used instead of the polyamino acid derivative obtained in Example 1 to obtain a surface-treated powder. This surface-treated powder was subjected to the same measurement and evaluation as in Example 13. The results are shown in Table 1 below.

Comparative Example 1

Example 13 was repeated except that lauric acid (supplied by Junsei Kagaku) was used instead of the polyamino acid derivative obtained in Example 1 to obtain a surface-treated powder. This surface-treated powder was subjected to the same measurement and evaluation as in Example 13. The results are shown in Table 1 below.

Comparative Example 2

Example 13 was repeated except that the polyamino acid derivative obtained in Example 1 was not used to obtain a surface-treated powder. This surface-treated powder was subjected to the same measurement and evaluation as in Example 13. The results are shown in Table 1 below.

TABLE 1

| | Surface-treated powder | |
|---|---|---|
| | Oil absorption | Moist touch |
| Example 13 | 14 | ⊚ |
| Example 14 | 15 | ⊚ |
| Example 15 | 16 | ⊚ |
| Example 16 | 15 | ○ |
| Comparative Example 1 | 15 | x |
| Comparative Example 2 | 25 | Δ |

Evaluation as a Dispersant

A typical paint formulation is shown in Table 2 below.

TABLE 2

| Paint formulation | |
|---|---|
| 50% emulsion resin | 100 parts |
| titanium dioxide | 70 |
| calcium carbonate | 200 |
| water | 100 |
| dispersant (polyamino acid derivative) | 2 (*) |
| defoamer | 1 |
| thickener (10% aqueous solution) | 20 |
| freeze-thaw stabilizer | 1 |
| film-forming aid | 1 |

*: value calculated as (i.e., in terms of) the solid content

Examples 17–23

Titanium dioxide "TIPAQUE CR-50" (supplied by Ishihara Sangyo) or carbon black "MA-100" (supplied by Mitsubishi Chemical) as the pigment, "Tylose H10000P" (supplied by Hoechst Gosei, nonvolatile content=1%) as the thickener, "SURFYNOL 104H" (supplied by Nisshin Kagaku; nonvolatile content=75%) as the defoamer, the polyamino acid derivative produced in each of Examples 1, 4 and 7–9 as the dispersant (provided in Example 21, the surface-treated powder of titanium dioxide (pigment) of the present invention produced in Example 13 was used instead of directly using the polyamino acid derivative of the present invention as the dispersant) and water (deionized water) were compounded in amounts shown in Table 3 below. These were uniformly mixed using a homomixer (supplied by Tokushu Kika Kogyo). Then, the pigment dispersion was conducted using a paint shaker (supplied by Red Devil) to give a pigment base.

With respect to the resulting pigment base, the viscosity (6 and 60 rpm) at 20° C. was measured using a B-type viscometer, and a thixotropy index value (TI value) (6/60 rpm) was obtained from this viscosity values, and the viscosity ratio was used as an index of rheological characteristics (grasp of the viscosity and the Theological characteristics). The results of the measurement are also shown in Table 3.

Subsequently, the above-obtained pigment base was used, and compounded with "VONCOAT 3990" (supplied by Dainippon Ink And Chemicals, Inc.; nonvolatile content= 50%) as the acrylic emulsion resin, ethylene glycol and butyl cellosolve as the solvent in amounts shown in Table3. These were uniformly mixed using a homomixer (supplied by Tokushu Kika Kogyo) while being stirred to obtain a paint composition (emulsion paint).

Further, the resulting paint composition was coated using a bar coater on a glass plate degreased with acetone, and dried at room temperature. Thereafter, the appearance of the coated film was evaluated according to JIS K5400 7.1 (grasp of properties of the coated film). The results of the evaluation are also shown in Table 3.

Evaluation of Toiletries (1)—Evaluation of Hair Care Products

Examples 24 and 25, and Comparative Examples 7 and 8

Each of the toiletries (four types) having the compositions shown in Table 4 below was spread on the hair in an amount

TABLE 3

|  | Paints | | | | | | | | | | |
|---|---|---|---|---|---|---|---|---|---|---|---|
|  | Examples | | | | | | | Comparative Examples | | | |
|  | 17 | 18 | 19 | 20 | 21 | 22 | 23 | 3 | 4 | 5 | 6 |
| polyamino acid derivative (*1) | Example 1 | Example 4 | Example 7 | Example 9 | — | Example 8 | Example 9 | — | — | — | — |
| Pigment base formulation | | | | | | | | | | | |
| titanium oxide (*2) | 60.0 | 60.0 | 60.0 | 60.0 | 60# | 0.0 | 0.0 | 60.0 | 60.0 | 0.0 | 0.0 |
| carbon black (*3) | 0.0 | 0.0 | 0.0 | 0.0 | 0.0 | 15.0 | 15.0 | 0.0 | 0.0 | 15.0 | 15.0 |
| thickener (*4) | 20.0 | 20.0 | 20.0 | 20.0 | 20.0 | 20.0 | 20.0 | 20.0 | 20.0 | 20.0 | 20.0 |
| defoamer (*5) | 0.2 | 0.2 | 0.2 | 0.2 | 0.2 | 0.2 | 0.2 | 0.2 | 0.2 | 0.2 | 0.2 |
| polyamino acid derivative (*6) | 0.6 | 0.6 | 0.6 | 0.6 | — | 0.6 | 0.6 | 0.0 | 0.0 | 0.0 | 0.0 |
| "DEMOL N" (*7) | 0.0 | 0.0 | 0.0 | 0.0 | 0.0 | 0.0 | 0.0 | 0.6 | 0.0 | 0.0 | 0.0 |
| "DISCOAT N-14" (*8) | 0.0 | 0.0 | 0.0 | 0.0 | 0.0 | 0.0 | 0.0 | 0.0 | 0.0 | 0.6 | 0.0 |
| deionized water | balance | balance | balance | balance | balance | balance | balance | balance | balance | balance | balance |
| Total | 100.0 | 100.0 | 100.0 | 100.0 | 100.0 | 100.0 | 100.0 | 100.0 | 100.0 | 100.0 | 100.0 |
| Viscosity (20° C.) | | | | | | | | | | | |
| 60 rpm (ps) | 102.0 | 80.0 | 70.4 | 65.0 | 50.0 | 16.0 | 15.5 | 150.0 | 200.0 | 50.0 | 160.0 |
| 6 rpm (ps) | 250.0 | 180.0 | 160.0 | 170.0 | 95.0 | 73.2 | 65.3 | 500.0 | 880.0 | 320.0 | 1230.0 |
| TI value (6/60 rpm) | 2.5 | 2.3 | 2.3 | 2.6 | 1.9 | 4.6 | 4.2 | 3.3 | 4.4 | 6.4 | 7.7 |
| Emulsion paint formulation | | | | | | | | | | | |
| pigment base | 52.6 | 52.6 | 52.6 | 52.6 | 52.6 | 28.0 | 28.0 | 52.6 | 52.6 | 28.0 | 28.0 |
| acrylic emulsion (*9) | 42.2 | 42.2 | 42.2 | 42.2 | 42.2 | 66.8 | 66.8 | 42.2 | 42.2 | 66.8 | 66.8 |
| ethylene glycol | 4.2 | 4.2 | 4.2 | 4.2 | 4.2 | 4.2 | 4.2 | 4.2 | 4.2 | 4.2 | 4.2 |
| butyl cellosolve | 1.0 | 1.0 | 1.0 | 1.0 | 1.0 | 1.0 | 1.0 | 1.0 | 1.0 | 1.0 | 1.0 |
| Total | 100.0 | 100.0 | 100.0 | 100.0 | 100.0 | 100.0 | 100.0 | 100.0 | 100.0 | 100.0 | 100.0 |
| Condition of coated film | good | good | good | good | good | good | good | slightly bad | bad | slightly bad | bad |

Footnote to Table 3
(*1): produced in Examples 1, 4 and 7–9 (numerical values calculated as, or in terms of, the solid content)
(*2): "TIPAQUE CR-50" supplied by Ishihara Sangyo
(*3): "MA-100" supplied by Mitsubishi Chemical
(*4): "Tylose H10000P" supplied by Hoechst Gosei (solid content: 1%)
(*5): "SURFYNOL 104H" supplied by Nisshin Kagaku (solid content: 70%)
(*6): produced in Examples 1, 4 and 7–9
(*7): supplied by Kao (solid content: 100%)
(*8): supplied by Dai-ichi Kogyo (solid content: 23%)
(*9): "VONCOAT 3990" supplied by Dainippon Ink And Chemicals (solid content: 50%)
surface-treated titanium dioxide powder produced in Example 13

Comparative Examples 3–6

In these Comparative Examples, the polyamino acid derivative of the invention was not used as a dispersant, and an ordinary dispersant was used.

That is, titanium oxide "TIPAQUE CR-50" or carbon black "MA-100" was used as a pigment, and "DEMOL N" or "DISCOAT N-14" was used or not used as a dispersant. These were mixed in amounts shown in Table 3, and pigment bases were obtained in the same manner as in Examples 17 to 23. Paint compositions (emulsion paints) were obtained therefrom. The properties of these pigment bases and paint compositions were also measured, and the results are shown in Table 3.

of 0.5 g per 10 g of the hair, and then, the moist touch, the gloss, the arrangement and the treatment effect upon the hair were evaluated. With respect to the treatment effect, the cold-waved hair was used, and the hair of which the ends were free from a dry and loose touch was evaluated to have a treatment effect. For the sake of comparison, cationic cellulose "LEOGARD GP" (supplied by Lion) was used.

The evaluation was conducted according to the following five grades.

⊚: good

○: slightly good

Δ: equivalent x: slightly poor xx: poor

The results of the evaluation are also shown in Table 4.

TABLE 4

Test on hair

|  | Ex. 24 | Ex. 25 | Comp. Ex. 7 | Comp. Ex. 8 |
|---|---|---|---|---|
| Composition (%) | | | | |
| polyamino acid derivative (*1) | 0.2 | 0.2 | 0 | 0 |
| polyamino acid derivative used | Ex. 8 | Ex. 9 | — | — |
| cationic cellulose (85% aqueous solution) (*2) | 0 | 0 | 0.24 | 0 |
| sodium laurylpolyoxyethylene (3)sulfate (25% aqueous solution) (*3) | 42 | 42 | 42 | 42 |
| lauroyldiethanolamide (*4) | 3 | 3 | 3 | 3 |
| lauryl dimethylaminoacetic acid betaine (26% aqueous solution) (*5) | 9.4 | 9.4 | 9.4 | 9.4 |
| methyl paraben | 0.2 | 0.2 | 0.2 | 0.2 |
| purified water | 45.18 | 45.18 | 45.14 | 45.38 |
| Effects | | | | |
| Moist touch | ◎ | ◎ | ○ | Δ |
| Gloss | ○ | ○ | Δ | Δ |
| Arrangement | ◎ | ○ | ○ | Δ |
| Treatment effect | ○ | ◎ | Δ | Δ |

(*1): value calculated as, or in terms of, the solid content
(*2): "LEOGARD GP (85% aqueous solution)" (Lion)
(*3): "EMAL 20C (25% aqueous solution)" (Kao)
(*4): "AMISOL LDE (solid content: 100%) (Kawaken Fine Chemical)
(*5): "AMPHITOL 24B (26% aqueous solution" (Kao)

Evaluation of Toiletries (2)—Evaluation as Moist Toiletries

Examples 26 and 27, and Comparative Example 9

Each of toiletries (three types) having compositions shown in Table 5 below was spread on the skin, and the change in the touch (imparting the moist touch) was observed. The evaluation was conducted according to the following five grades.

◎: good
○: slightly good
Δ: moderate
x: poor
xx: very poor

The results of the evaluation are also shown in Table 5.

TABLE 5

Moistness

|  | Ex. 26 | Ex. 27 | Comp. Ex. 9 |
|---|---|---|---|
| Composition (%) | | | |
| polyamino acid derivative of Example 1 (*1) | 3.0 | | |
| polyamino acid derivative of Example 5 (*1) | | 3.0 | |
| propylene glycol | 2.0 | 2.0 | 2.0 |
| carboxymethyl cellulose (*2) | 0.2 | 0.2 | 0.2 |
| methyl paraben | 0.2 | 0.2 | 0.2 |
| sodium benzoate | 0.1 | 0.1 | 0.1 |
| purified water | 94.5 | 94.5 | 97.5 |
| Total | 100 | 100 | 100 |
| Effects | | | |
| Moist touch | ◎ | ◎ | Δ |

(*1): value calculated as the solid content
(*2): "HONESTGUM" supplied by Daicel Chemical Industries Evaluation as a Chelating Agent Examples 28–34, and Comparative Examples 10–13

1.1 Gram of calcium chloride (supplied by Junsei Kagaku) was dissolved in, and filled up with, distilled water to 10 ml. To this was added 10 mg (calculated as or in terms of the solid content) of a chelating agent including each of the polyamino acid derivatives shown in Tables 6 and 7. The resulting mixture was adjusted in volume to 90 ml with the addition of distilled water. 1.42 Gram of sodium sulfate (supplied by Junsei Kagaku) was dissolved in, and filled up with, distilled water to 10 ml, and this solution was added to the above-mentioned mixed solution while being stirred. The weight of the precipitate formed was measured. The results of the measurement are also shown in Tables 6 and 7. By the way, the smaller the amount of the precipitate is, the higher the chelating force is.

TABLE 6

Chelating force

|  | Chelating agent | Molecular weight (NMR spectroscopy) | Number of glutamic acids per molecule (*2) | Amount of sodium hydroxide used (*3) | pH adjustment | Speed of dropwise addition of epichlorohydrin | Chelating force (weight of precipitate (g)) |
|---|---|---|---|---|---|---|---|
| Ex. 28 | Ex. 1 (*1) | 850 | 3.4 | 2 | no | high | 0.050 |
| Ex. 29 | Ex. 2 | 3000 | 12.1 | 3 | yes | low | 0.008 |
| Ex. 30 | Ex. 10 | 1800 | 7.3 | 3 | yes | high | 0.009 |
| Ex. 31 | Ex. 12 | 880 | 3.6 | 3 | no | high | 0.049 |
| Comp. Ex. 10 | Ex. 11 | 550 | 2.2 | 2 | no | very high | 0.150 |

TABLE 6-continued

Chelating force

| Chelating agent | Molecular weight (NMR spectroscopy) | Number of glutamic acids per molecule (*2) | Amount of sodium hydroxide used (*3) | pH adjustment | Speed of dropwise addition of epichlorohydrin | Chelating force (weight of precipitate (g)) |
|---|---|---|---|---|---|---|

(*1): For example, Example 1 shows that the chelating agent is the polyamino acid derivative formed in Example 1.
(*2): numerical values calculated from the molecular weight measured by the NMR spectroscopy.
(*3): amount (mols) of sodium hydroxide per mol of glutamic acid

TABLE 7

Chelating force (continued)

| | Chelating agent | Molecular weight (NMR spectroscopy) | Number of amino acids per molecule (*2) | Chelating force (weight of precipitate (g)) |
|---|---|---|---|---|
| Ex. 32 | Ex. 3 (*1) | 4500 | 20.1 | 0.002 |
| Ex. 33 | Ex. 5 | 880 | 3.6 | 0.025 |
| Ex. 34 | Ex. 7 | 1600 | 4.3 | 0.004 |
| Comp. Ex. 11 | "CHELEST 400" (*3) | — | — | 1.12 |
| Comp. Ex. 12 | "CHELEST 700" (*4) | — | — | 1.10 |
| Comp. Ex. 13 | — | — | — | 1.23 |

(*1): For example, Example 3 shows that the chelating agent is the polyamino acid derivative formed in Example 3.
(*2): value calculated from the molecular weight measured by the NMR spectroscopy.
(*3): tetrasodium ethylenediamine tetraacetate.tetrahydrate supplied by Chelest
(*4): trisodium nitrilotriacetate.monohydrate supplied by Chelest

Evaluation as a Rust-proofing Agent

Examples 35–38, and Comparative Example 14

A test piece of a general steel material (according to JIS G3108) for cold finished steel bars was washed with isooctane. Thereafter, this was preliminarily polished with a polishing cloth No. 150 and then with a polishing cloth No. 280 (according to JIS R6521). 0.33 Gram (as the solidcontent) of each of the amino acid derivatives obtained in Examples 1–3 and 10 was mixed with 330 ml of tap water. The test piece polished was dipped in the solution, and allowed to stand at 60° C. for 1 hour. The occurrence of rust was observed, and evaluated according to the following three grades.

(1) Low degree: The number of rust spots having a diameter of 1 mm or less on the surface of the test piece does not exceed 6.
(2) Medium degree: The number of rust spots exceeds in (1), and rust is observed on 5% or less of the surface of the test piece.
(3) High degree: Rust is observed on more than 5% of the surface of the test piece.

The results are shown in Table 8.

TABLE 8

| | Rust-proofing agent | Molecular weight (NMR spectroscopy) | Number of glutamic acids per molecule (*2) | Amount of sodium hydroxide used (*3) | pH adjustment | Speed of dropwise addition of epichlorohydrin | Rust-proofing property |
|---|---|---|---|---|---|---|---|
| Ex. 35 | Ex. 2 (*1) | 3000 | 12.1 | 3 | yes | low | low degree (5% or less) |
| Ex. 36 | Ex. 3 | 4500 | 20.1 | 3 | yes | low | low degree (5% or less) |
| Ex. 37 | Ex. 10 | 1800 | 7.3 | 3 | yes | high | low degree (5% or less) |
| Ex. 38 | Ex. 1 | 850 | 3.4 | 2 | no | high | high degree (50%) |

TABLE 8-continued

| Rust-proofing agent | Molecular weight (NMR spectroscopy) | Number of glutamic acids per molecule (*2) | Amount of sodium hydroxide used (*3) | pH adjustment | Speed of dropwise addition of epichlorohydrin | Rust-proofing property |
|---|---|---|---|---|---|---|
| Comp. Ex. 14 | — | — | — | — | — | high degree (100%) |

(*1): For example, Example 2 shows that the rust-proofing agent is the polyamino acid derivative formed in Example 2.
(*2): value calculated from the molecular weight measured by the NMR spectroscopy.
(*3): amount (mols) of sodium hydroxide per mol of glutamic acid

Effects of the Invention

As stated above, the polyamino acid derivative according to the present invention is excellent as a dispersant, a chelating agent for metallic ions and a rust-proofing agent. Further, a powder surface-treated with this polyamino acid derivative is improved in the water repellency. When it is incorporated in toiletries, the moist touch, the gloss, the easy arrangement and the treatment effect can be imparted to the hair, and the moist touch to the skin.

What is claimed is:

1. A polyamino acid derivative comprising at least four amino acid molecules, bound by crosslinking groups through their nitrogen atoms according to the following structure:

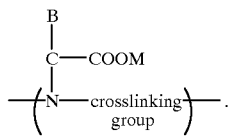

2. The polyamino acid derivative of claim 1, wherein the crosslinking group is an alkylene group, an alkylene group which has a hydroxyl group on the carbon chain, an alkylene group having an ether linkage in the carbon chain, or an alkylene group that has both a hydroxyl group on, and an ether linkage in the carbon chain.

3. The polyamino acid derivative of claim 2, wherein the alkylene groups are selected from the group consisting of Formulas (1), (2) and (3) below:

(1)

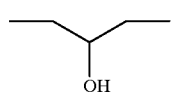

(2)

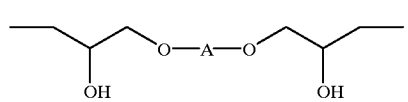

(3)

wherein k in Formula (1) is an integer of from 1 to 10, and A in Formula (3) is a group represented by any one of Formulas (4)–(6) below:

(4)

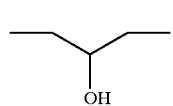

(5)

wherein j in Formula (4) is an integer of from 1 to 10, and m in Formula (6) is an integer of from 1 to 15.

4. A polyamino acid derivative of claim 1, comprising any one of Formulas (7), (8) or (9) below:

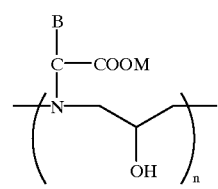

(7)

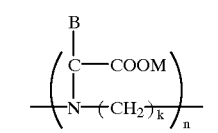

(8)

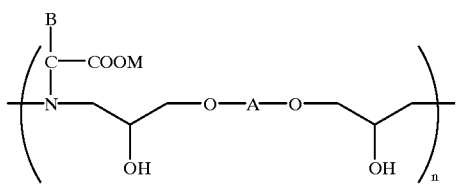

(9)

wherein B is an amino acid side chain,

M is a hydrogen atom or a counter ion, n is an integer of 4 or more, k is an integer of from 1 to 10, and A is any one of Formulas (4), (5) or (6) below:

(4)

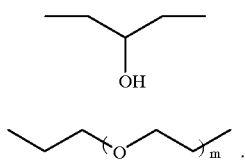

5. The polyamino acid derivative of claim 1, produced by reacting epichlorohydrin and/or a polyepoxy compound with an amino acid, wherein said amino acid is present in an amount ranging from $2/3 \times (x+y \times z/2)$ to $4/3 \times (x+y \times z/2)$ moles, wherein x is the number of moles of epichlorohydrin and y is the number of moles of the polyepoxy compound having z epoxy functional groups.

6. The polyamino acid derivative as set forth in claim 5, wherein the polyepoxy compound is polyglycidyl ether.

7. The polyamino acid derivative as set forth in claim 5, wherein said reacting is performed in the presence of an amine compound.

8. The polyamino acid derivative as set forth in claim 1, wherein the number average molecular weight measured by the NMR spectrometry is 100,000 or less.

9. A chelating agent comprising the polyamino acid derivative of claim 1.

10. A pigment dispersant comprising the polyamino acid derivative of claim 1.

11. A powder which is surface-treated with a polyamino acid derivative of claim 1.

12. A toiletry comprising the polyamino acid derivative of claim 1.

13. A rust-proofing agent comprising the polyamino acid derivative of claim 1.

14. A pigment dispersant, a surface-treated powder, a toiletry, or a rust-proofing agent comprising the polyamino acid derivative of claim 2.

15. A pigment dispersant, a surface-treated powder, a toiletry, or a rust-proofing agent comprising the polyamino acid derivative of claim 3.

16. A pigment dispersant, a surface-treated powder, a toiletry, or a rust-proofing agent comprising the polyamino acid derivative of claim 1, wherein the number average molecular weight of the polyamino acid derivative, as measured by NMR spectrometry, is 100,000 or less.

* * * * *

UNITED STATES PATENT AND TRADEMARK OFFICE
CERTIFICATE OF CORRECTION

PATENT NO.    : 6,291,634 B1
DATED         : September 18, 2001
INVENTOR(S)   : Hiroyuki Tanaka et al.

It is certified that error appears in the above-identified patent and that said Letters Patent is hereby corrected as shown below:

Title page,
Item [57], ABSTRACT,
Line 9, "asid", should read -- acid --.

Column 3,
Line 24, "synthsis" should read -- synthesis --.

Column 13,
Line 46, "ref lux" should read -- reflux --.
Line 67, "ref lux" should read -- reflux --.

Column 16,
Line 11, "ref lux" should read -- reflux --.
Line 53, "ref lux" should read -- reflux --.

Column 17,
Line 8, "70Parts" should read -- 70 Parts --.

Column 18,
Line 57, "Theological" should read -- rheological --.

Column 23,
Line 45, "solidcontent" should read -- solid content --.

UNITED STATES PATENT AND TRADEMARK OFFICE
CERTIFICATE OF CORRECTION

PATENT NO. : 6,291,634 B1
DATED : September 18, 2001
INVENTOR(S) : Hiroyuki Tanaka et al.

It is certified that error appears in the above-identified patent and that said Letters Patent is hereby corrected as shown below:

Column 26,
Line 27, please insert below formula 5 formula 6 as follows:

--
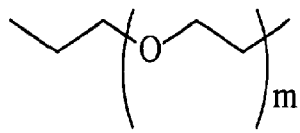   (6)

--

Signed and Sealed this

Sixteenth Day of July, 2002

Attest:

JAMES E. ROGAN
Attesting Officer   Director of the United States Patent and Trademark Office